United States Patent
Hakim et al.

(10) Patent No.: US 8,848,170 B2
(45) Date of Patent: Sep. 30, 2014

(54) OPTICAL DETECTOR

(75) Inventors: Christophe Jean Erez Hakim, Mountain View, CA (US); Geoffrey Byron Noakes, Jr., Arlington, VA (US)

(73) Assignee: Silicon Laboratories Inc., Austin, TX (US)

( * ) Notice: Subject to any disclaimer, the term of this patent is extended or adjusted under 35 U.S.C. 154(b) by 295 days.

(21) Appl. No.: 13/342,255

(22) Filed: Jan. 3, 2012

(65) Prior Publication Data

US 2013/0169947 A1    Jul. 4, 2013

(51) Int. Cl.
*G01C 3/08* (2006.01)

(52) U.S. Cl.
USPC .......... 356/3.1; 356/3.01; 356/4.01; 356/5.01

(58) Field of Classification Search
USPC ............. 356/3.01–3.15, 4.01–4.1, 5.01–5.15, 356/6–22, 28, 28.5
See application file for complete search history.

(56) References Cited

U.S. PATENT DOCUMENTS 5,082,364 A * 1/1992 Russell .................. 356/5.15

* cited by examiner

*Primary Examiner* — Luke Ratcliffe (74) *Attorney, Agent, or Firm* — Trop, Pruner & Hu, P.C.

(57) ABSTRACT

A technique includes using at least one emitter to generate a first optical signal to propagate along a first optical path to interact with a target, to generate a second optical signal and generate a third optical signal to propagate along a second optical path other than the first optical path to generate a fourth optical signal. The technique includes using at least one receiver to acquire a first measurement of the second optical signal and acquire a second measurement of the fourth optical signal. The technique includes generating an indication of a parameter that is associated with a target, which includes scaling a ratio of the first and second measurements based at least in part on optical communication between the emitter(s) and the receiver(s) that does not involve interaction with the target.

20 Claims, 6 Drawing Sheets

OPTICAL DETECTOR

BACKGROUND

A proximity detector may be used to measure a distance to a given target. The measured distance, in turn, may be used for a number of different purposes such as industrial automation, consumer electronics, security panels, etc. A typical optical proximity detector includes an emitter, such as a light emitting diode (LED), which emits an optical signal that reflects from the target to produce a corresponding reflected optical signal. The reflected optical signal, in turn, is detected by the proximity detector's receiver, such as a photodiode. In general, when the target is relatively large, as compared to the desired detection distance, the amount of light reflected from the target is inversely proportional to the square of the distance between the proximity detector and the target.

SUMMARY

In an example embodiment, a technique includes using at least one emitter to generate a first optical signal to propagate along a first optical path to interact with a target to generate a second optical signal, and generate a third optical signal to propagate along a second optical path other than the first optical path to generate a fourth optical signal. The technique includes using at least one receiver to acquire a first measurement of the second optical signal, and acquire a second measurement of the fourth optical signal. The technique includes generating an indication of a parameter that is associated with a target, which includes scaling a ratio of the first and second measurements based at least in part on optical communication between the emitter(s) and the receiver(s) that does not involve interaction with the target.

In another example embodiment, an optical detector includes at least one emitter, at least one receiver and a controller. The emitter(s) generate a first optical signal to propagate along a first optical path to interact with an object to generate a second optical signal, and generate a third optical signal to propagate along a second optical path other than the first optical path to generate a fourth optical signal. The receiver(s) acquire a first measurement of the second optical signal and acquire a second measurement of the fourth optical signal. The controller scales a ratio of the first and second measurements based at least in part on at least one additional measurement acquired by the receiver(s), which does not involve interaction with the object to generate an indication of a parameter that is associated with the object.

In yet another example embodiment, an apparatus includes an integrated circuit that includes a controller, at least one driver, and at least one receiver. The driver(s) are adapted to generate at least one electrical signal to generate a first optical signal to propagate along a first optical path to interact with an object to generate a second optical signal, and generate a third optical signal to propagate along a second optical path other than the first optical path to generate a fourth optical signal. The receiver(s) receive at least one electrical signal, which is indicative of a first measurement of the second optical signal, and a second measurement of the fourth optical signal. The controller is adapted to scale a first ratio of the first and second measurements based at least in part on optical crosstalk communication between the emitter(s) and the receiver(s) to generate an indication of a parameter that is associated with the object.

Advantages and other desired features will become apparent from the following drawings, description and claims.

DETAILED DESCRIPTION

Figure 1:
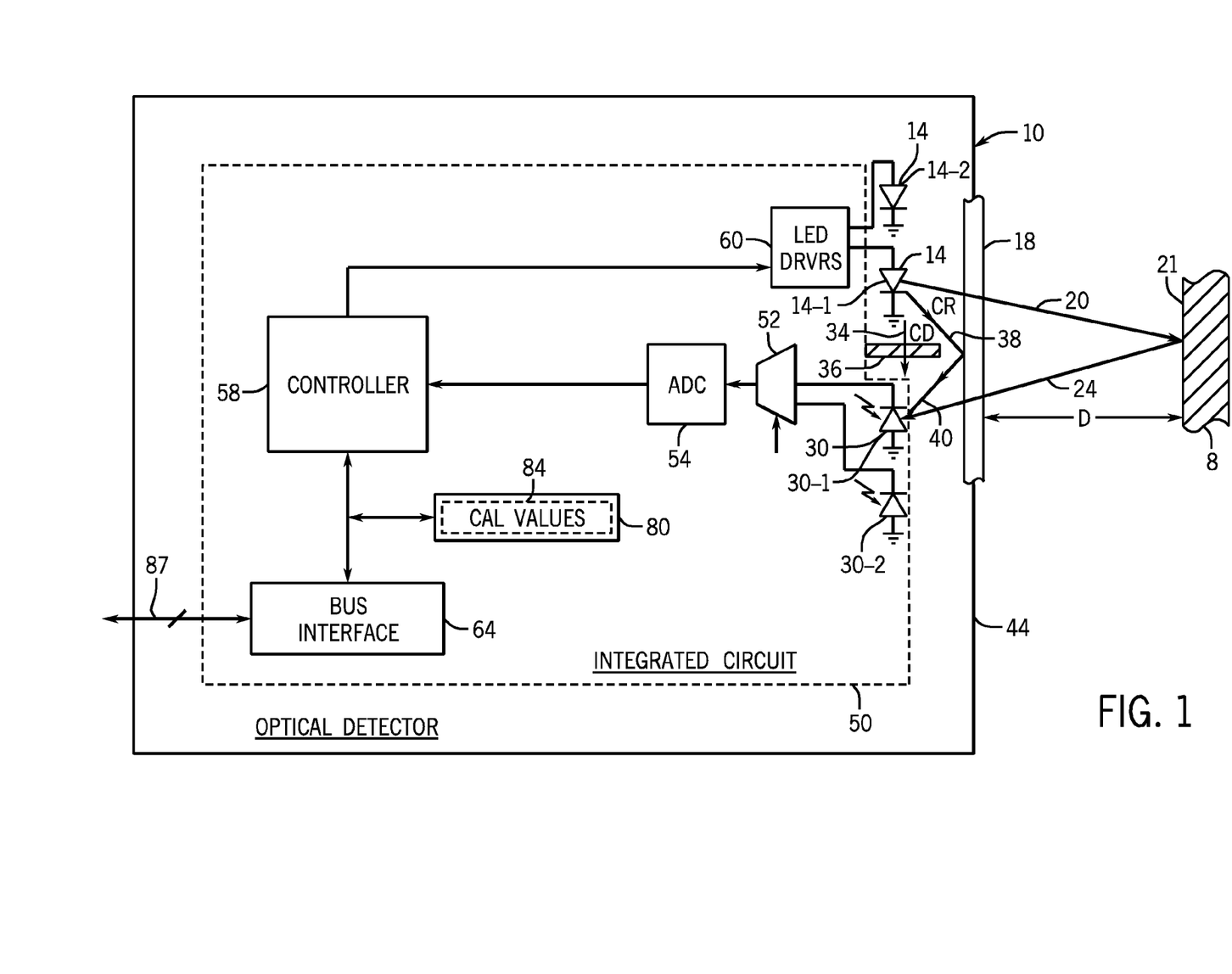
FIG. 1 is a schematic diagram of an optical detector according to an example embodiment.

Referring to FIG. 1, in accordance with example embodiments disclosed herein, an optical detector 10 generates and detects optical signals for purposes of acquiring a measurement that is indicative of an optical interaction with an object, or target 8, of interest and in general, may be used to derive an indicator for a parameter that is associated with the target 8. For example, the optical detector 10 may be a proximity detector that measures at least one distance (an exemplary distance "D" being depicted in FIG. 1) between the optical detector 10 and the target 8. As a non-limiting example, for this purpose, the optical detector 10 may generate an incident optical signal, which propagates along an optical path segment 20 and interacts with a surface 21 of the target 8 (reflects from the surface 21, for example) to produce a corresponding reflected optical signal, which propagates along an optical path segment 24 back to the optical detector 10 for measurement. The optical detector 10 may process the measurement for purposes of determining an indicator of the distance D.

Alternatively, as another non-limiting example, the optical detector 10 may be a particle density detector that detects the particle density of the target 8. In this manner, for this example, the target 8 may be a fluid (gas or liquid) that has particles (suspended particles, for example), which have a density that is measurable using the optical detector 10. Measurement of the reflected optical signal may be used to derive an indicator for the density of the particles, as the incident optical signal interacts with the fluid to generate the optical signal that propagates along the optical path segment 24 to the optical detector 10. In other words, the optical signal that propagates along the optical path segment 24 is the result of the reflection of the incident optical signal from the fluid and/or the partial obstruction of the incident optical signal by the fluid. As a more specific non-limiting example, the optical detector 10 may be part of a smoke detector that detects the particle density of air that enters a sensing chamber, or cage, of the smoke detector. By sensing the particle density of the air within the cage, a determination may be made whether the chamber contains a concentration of smoke that is sufficient to trigger an alarm.

Thus, in general, the optical detector 10 may be used in numerous applications to measure an optical interaction with a target (a solid, a gas or a liquid) for purposes of generating an indicator of a parameter (distance to the target or a particle density of the target, as non-limiting examples) that is associated with the target.

As disclosed further herein, optical detector's measurement of the optical signal that propagates along the optical path segment 24 contains a component that is attributable to the optical signal and components that may be attributed to optical crosstalk communication between the detector's emitter and receiver. Moreover, the optical detector's sensing of these optical components may be influenced by such factors as emitter efficiency variations, emitter driver variations and detector conversion-factor variations.

In accordance with example embodiments, in general, the optical detector 10 includes at least one emitter 14 (emitters 14-1 and 14-2 being depicted in FIG. 1, as non-limiting examples), such as a light emitting diode (LED). The optical detector 10 controls the emitter(s) 14 to emit incident light to allow at least one receiver 30 (receivers 30-1 and 30-2 being depicted in FIG. 1, as non-limiting examples) of the optical detector 10, such as a photodiode, to acquire measurements of the reflected light.

The optical detector 10 may be used to determine multiple parameters that are associated with the target 8. For example, in some embodiments, the optical detector 10 may determine indicators for multiple distances to a given target for purposes of employing triangulation to determine a two dimensional or three dimensional location of the target. For purposes of simplifying the following discussion, it is assumed that the optical detector 10 is used to determine an indicator for a single parameter that is associated with the target 8. However, in accordance with other embodiments, the optical detector 10 may be used to determine indicators for multiple distance measurements (when the optical detector 10 is used as a proximity detector, for example) or multiple measurements associated with a particle density of the target 8 (such as when the optical detector 10 is used in a smoke detector, for example). Thus, many variations are contemplated and are within the scope of the appended claims.

The light that is sensed by a given receiver 30 of the optical detector 10 contains optical components, other than the light that is produced solely by the optical signal that propagates along the optical path segment 24. First, the light contains ambient light, which is sensed by the optical detector 10 during times when measurements are not being made and is removed by the detector 10. For purposes of simplifying the following discussion, it is assumed that the optical detector 10 has taken appropriate measures to compensate the measurements to remove the ambient light components from these measurements; and thus, the acquired measurements discussed herein do not contain ambient light components. For example, in accordance with some embodiments, the ambient light component is cancelled by measuring ambient light without activating any emitter and then subtracting this measurement from measurements that measure emitter light (and ambient light), thereby removing the ambient light component.

A given receiver 30 of the optical detector 10 also senses light, which is attributable to optical crosstalk communication between the emitter 14 and the receiver 30. More specifically, the optical crosstalk communication includes a direct crosstalk component (called the "direct crosstalk $C_D$" herein), which represents direct optical coupling (represented by an optical path segment 34 in FIG. 1) between the emitter 14 and the receiver 30. In this manner, although the optical detector 10 may include an optical isolator, or blocker 36, to attenuate the direct optical crosstalk, the optical isolation may be imperfect, thereby giving rise to the direct crosstalk component $C_D$.

The optical crosstalk communication also contains an indirect crosstalk component (called the "$C_R$ component" herein), which occurs when light takes an indirect path between the emitter 14 and the receiver 30 by reflecting from, for example, surfaces of the optical detector 10, which may or may not be inherent to the proximity or particle density detection function. For the example that is depicted in FIG. 1, the indirect crosstalk component $C_R$ is shown as arising from optical communication between the emitter 14 and the receiver 30 due to light that propagates from the emitter 14 along an optical path segment 38 to a semi-transparent overlay or product cover, such as a window 18, where the light reflects to produce light that propagates along optical path segment 40 to the receiver 30.

As a result of the above-described direct and indirect optical crosstalk communication, the actual optical signal that is measured by the receiver 30 is a summation of three components: "$R+C_D+C_R$," where "R" represents the component that is attributable solely to the optical signal that propagates along the optical path segment 24.

As disclosed herein, the optical detector 10 compensates for several characteristics of the optical detector 10, which vary from one optical detector 10 to the next and which might make it challenging to remove the $C_D+C_R$ component. For example, the optical detector's emitter efficiency influences the measurement of these components, and the emitter efficiency varies from one optical detector to the next, due to such factors as manufacturing tolerances; temperature drift; and component aging, which are able to modify the received optical signal. Additionally, circuitry of the optical detector 10, which drives the emitter(s) 14 may introduce errors that are unknown or may not be controlled precisely, due to manufacturing variations, temperature drift and component aging. Moreover, the conversion of the detected optical signal from optical power to an intelligible analog or digital electrical signal may also vary with the manufacturing tolerances, temperature drift and component aging.

As described in U.S. patent application Ser. No. 13/172, 031, entitled "OPTICAL DETECTOR," which was filed on Jun. 29, 2011, the optical detector 10 may generate an indication (e.g., an analog or digital signal) of the optical component R by comparing a ratio of the measured optical signal (R+Cd+Cr) to a baseline ($C_D+C_R$), as set forth below:

$$(R+Cd+Cr)/(Cd+Cr) > \text{Threshold 1, or} \qquad \text{Eq. 1}$$

$$(R+Cd+Cr)/(Cd+Cr) < \text{Threshold 1,} \qquad \text{Eq. 2}$$

depending on the application's requirements, and where "Threshold 1" represents a predetermined detection threshold. In other words, the optical detector 10 may scale the acquired measurement based on a measure of optical crosstalk communication. As a non-limiting example, the Cd+Cr baseline may be derived from a measurement acquired by the optical detector 10 in the absence of a target.

Thus, a baseline formed from the $C_D$ and $C_R$ components may be used as a calibration variable to compensate the acquired optical measurement. Because all three of the R, $C_D$ and $C_R$ components vary proportionally with such factors as aging, manufacturing tolerances and temperature drift, the ratio that is set forth in each of Eqs. 1 and 2 generally cancels out the variations, the corresponding threshold (Threshold 2) is not adjusted for these variations, and the optical detector 10 therefore generates a relatively precise indication of the distance D to the target 8 or the particle density of the target 8.

Another way to generate an indicator for a particular parameter (distance or particle density, as non-limiting examples) that is associated with the target 8 is to optically interact with the target 8 using different optical paths between the optical detector 10 and the target 8; acquire optical measurements to measure these optical interactions; determine a detection ratio based on the optical measurements; determine a baseline ratio based on optical crosstalk communication that is associated with the optical measurements; and generate an indicator for the parameter (distance or particle density, for example) associated with the target 8 based on a ratio of the detection ratio to the baseline ratio. In this regard, in accordance with some embodiments, the optical detector 10 may drive one or more emitters 14 at different times to establish the different optical paths and use one or more of the receivers 30 to acquire the corresponding optical measurements.

Figure 2:
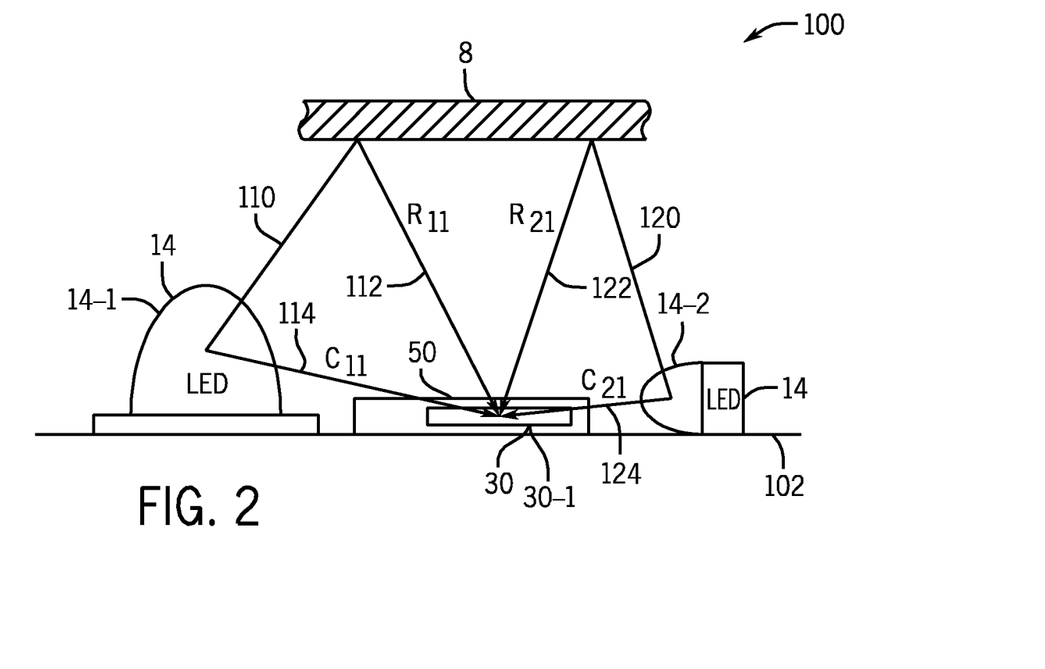
FIG. 2 is an example illustration of the use of two emitters and a receiver of the optical detector to acquire optical measurements using two optical paths according to an example embodiment.

As a more specific example, FIG. 2 depicts an example illustration 100 of two such optical paths that may be used by the optical detector 10 in accordance with some embodiments: 1.) a first optical path along which an incident optical signal propagates from the emitter 14-1 to the target 8 along an optical path segment 110, reflects from the target 8 to produce a reflected optical signal that propagates along an optical path segment 112 and is sensed by the receiver 30-1; and 2.) a second optical path along which a second incident optical signal propagates from the emitter 14-2 along an optical path segment 120, reflects from the target 8 to produce a reflected optical signal that propagates along an optical path segment 122 and is sensed by the receiver 30-1.

In this manner, emission of light for the different pathways and the corresponding measurements may be conducted in a time-multiplexed fashion (i.e., the optical detector 10 may, for example, sequentially use the optical paths in non-overlapping time intervals). Moreover, in some embodiments, one of the emitters 14 reflects relatively more light on the target 8, and the other emitter 14 (such as emitter 14-2) reflects relatively more light on the optical detector 10. As depicted in FIG. 2, one way to achieve this is through the use of an LED (the emitter 14-1, for this example) that is oriented in a direction that is generally aligned with the normal of a substrate 102 and the use of another LED (the emitter 14-2, for this example) that is oriented in a direction that is generally orthogonal with respect to the normal of the substrate 102. The two LEDs are assumed to have similar thermal properties with respect to output efficiency, and to be thermally coupled.

In the following notation, "$R_{11}$" represents an optical component that is attributable solely to the optical signal that propagates along the optical path segment 112; and "$R_{21}$" represents an optical component that is attributable solely to the optical signal that propagates along the optical path segment 122. The receiver 30-1 does not, however, measure only the $R_{11}$ and $R_{21}$ components. Instead, in addition to the $R_{11}$ optical component, the receiver 30-1 also acquires a measurement of an optical crosstalk component (called "$C_{11}$") that propagates along an optical path segment 114 as shown in FIG. 2. The $C_{11}$ component represents a combination of the indirect and direct optical crosstalk communication components associated with measuring the $R_{11}$ optical component. Likewise, the receiver 30-1 senses an optical crosstalk communication component (called "$C_{21}$") in addition to the $R_{21}$ optical component. As depicted in FIG. 2, the $C_{21}$ component propagates along an optical path segment 124 from the emitter 14-2. The $C_{21}$ component is associated with the direct and indirect optical crosstalk communication between the emitter 14-2 and the receiver 30-1.

Thus, during a given time interval, the optical detector 10 uses the emitter 14-1 and the receiver 30-1 to acquire a measurement of the $R_{11}$ and $C_{11}$ components; and in another given time interval, the optical detector 10 uses the emitter 14-2 and the receiver 30-1 to acquire a measurement of the $R_{21}$ and $C_{21}$ optical components.

In accordance with example embodiments, an indicator for a parameter that is associated with the target 8 may be determined by determining a ratio (called the "double ratio" herein) of 1. a ratio (called the "detection ratio" herein) of the two measurements acquired by the receiver 30 and 2. a ratio (called the "baseline ratio" herein), which is a ratio of the $C_{11}$ and $C_{21}$ optical components. The indicator for the parameter may be derived by comparing the double ratio to a predetermined threshold. More specifically, in accordance with example embodiments given the optical paths illustrated in FIG. 2, the optical detector 10 may determine the double ratio as follows:

$$\text{Double ratio} = \frac{\text{Detection ratio}}{\text{Baseline ratio}} = \frac{C_{21} \times (C_{11} + R_{11})}{C_{11} \times (C_{21} + R_{21})}. \qquad \text{Eq. 3}$$

Using this double ratio, in accordance with some embodiments, the optical detector 10 may determine an indicator of the parameter associated with the target 8 by performing one of the comparisons that are set forth below:

$$\text{,Double ratio} < \text{Threshold 2 and} \qquad \text{Eq. 4}$$

$$\text{,Double ratio} > \text{Threshold 2} \qquad \text{Eq. 5}$$

where "Threshold 2" represents a predetermined detection threshold. The use of Eq. 4 or Eq. 5 depends on the particular application in which the optical detector 10 is employed. In this manner, the optical detector 10 may use either Eq. 4 or 5, depending on whether the optical detector 10 is employed in an optically reflective or obstructive application.

A particular advantage of using the double ratio, such as the exemplary double ratio described above in Eq. 3, to derive an indicator of the parameter is that the temperature dependent of factors (LED efficiency and wavelength, as non-limiting examples) that may possibly otherwise affect the indicator is significantly minimized, if not eliminated. In particular, as compared to the technique described in Eq. 1 and Eq. 2, the double ratio technique is relatively immune to changes of temperature that may occur between the baseline measurement and the measurement of a target. This is apparent in Eq. 3, because proportional changes of calibration between the baseline measurement and the target measurement are cancelled out. Thus, if the emitters 14-1 and 14-2 (LEDs, for example) have similar thermal variations and are thermally coupled, both the baseline ratio $C_{11}/C_{21}$ and the measurement ratio $(C_{11}+R_{11})/(C_{21}+R_{21})$ are invariant as the temperature varies between the baseline measurement and the target measurement.

Figure 3:
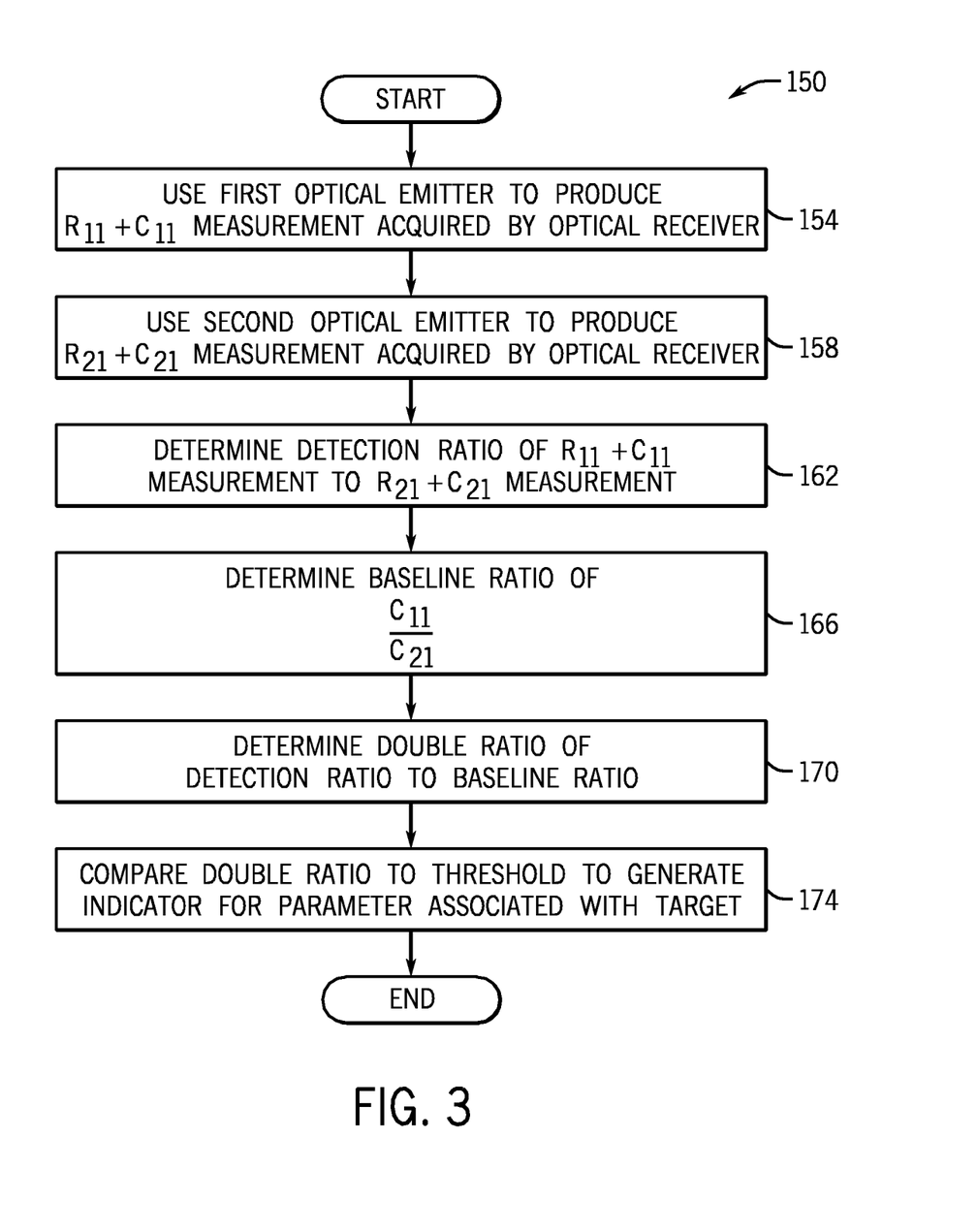
FIG. 3 is a flow diagram depicting a technique to generate an indicator for a parameter that is associated with a target using the optical paths of FIG. 2 according to an example embodiment.

Thus, a technique 150, which is depicted in FIG. 3, may be used for purposes of generating an indicator for a parameter that is associated with a target. Pursuant to the technique 150, a first optical emitter is used (block 154) to produce a measurement (i.e., a $R_{11}+C_{11}$ measurement), which is acquired by an optical receiver. A second optical emitter is used (block 158) to produce another measurement (i.e., a $R_{21}+C_{21}$ measurement), which is acquired by the optical receiver. A detection ratio (i.e., a ratio of the $R_{11}+C_{11}$ measurement to the $R_{21}+C_{21}$ measurement) is also determined, pursuant to block 162. A baseline ratio (e.g., $C_{11}/C_{21}$), is then determined, pursuant to block 166. The technique 150 includes determining a double ratio of the detection ratio to the baseline ratio, pursuant to block 170. An indicator for the parameter associated with the target may then be determined by comparing (block 174) the double ratio to a particular threshold.

Figure 4:
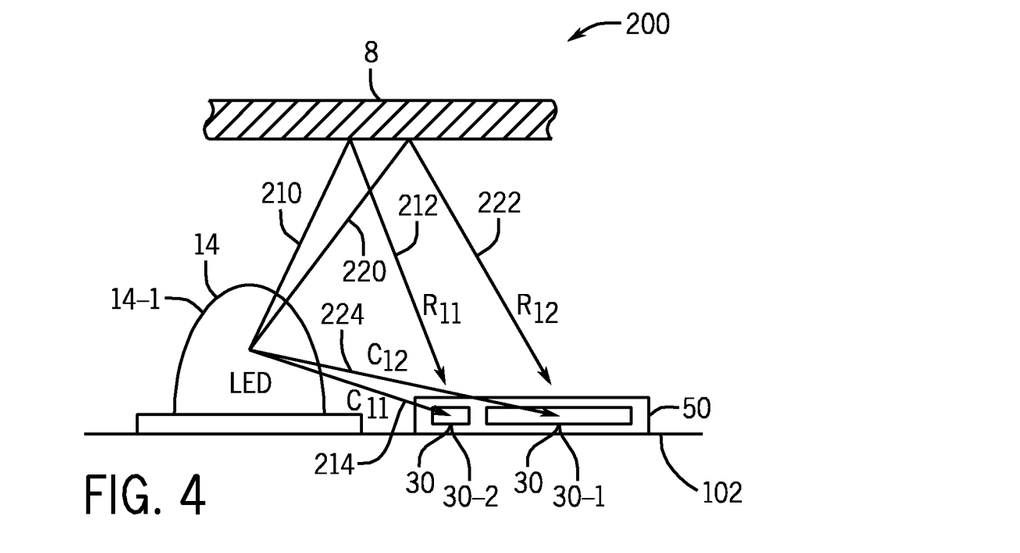
FIG. 4 is an example illustration of the use of an emitter and two receivers of the optical detector to acquire measurements using two optical paths according to an example embodiment.

Referring to FIG. 4, in accordance with some embodiments, an example illustration 200 depicts the creation and use of two optical paths by the optical detector 10 using a single emitter 14-1 and two optical receivers 30-1 and 30-2. Moreover, in accordance with some embodiments, one of the optical paths may be associated with relatively more reflected light from the target 8 than the other optical path.

For the first optical path, the emitter 14-1 emits an incident optical signal that propagates along an optical path segment 210 reflects from the target 8 to produce a reflected optical signal, which propagates along an optical path segment 212 is associated with an optical component $R_{11}$ and is sensed by the receiver 30-2. For the other optical path, the emitter 14-1 emits an incident optical signal that propagates along the optical path segment 220 reflects from a different portion of the target 8 to produce a reflected optical signal. This optical signal propagates along the optical path segment 222, is sensed by the receiver 30-1 and is associated with the optical component $R_{12}$. The measurement of the $R_{11}$ optical component also contains an optical crosstalk communication component $C_{11}$, which propagates from the emitter 14-1 to the receiver 30-2 along an optical path segment 214. The measurement of the $R_{12}$ optical component contains optical crosstalk communication component $C_{12}$, which propagates along an optical path segment 224 from the emitter 14-2 to the photodiode 30-1. The corresponding double ratio for the arrangement that is depicted in FIG. 4 may be described as follows:

$$\text{Double ratio} = \frac{\text{Detection ratio}}{\text{Baseline ratio}} = \frac{C_{12} \times (C_{11} + R_{11})}{C_{11} \times (C_{12} + R_{12})}. \quad \text{Eq. 6}$$

The optical detector 10 may compare the double ratio of Eq. 6 to a threshold (as set forth in Eqs. 4 and 5) for purposes of deriving an indicator for the parameter that is associated with the target 8.

Figure 5:
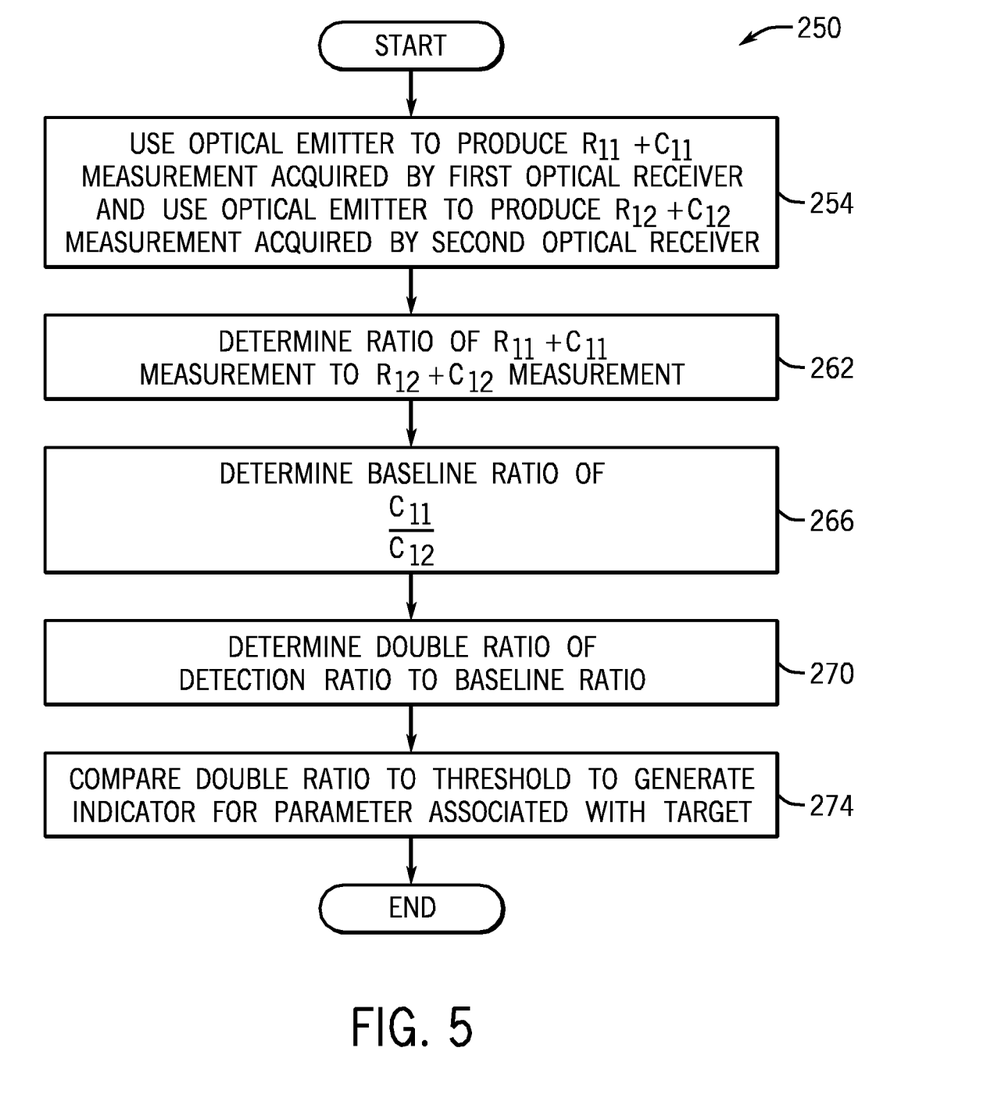
FIG. 5 is a flow diagram depicting a technique to determine an indicator for a parameter that is associated with a target using the optical paths of FIG. 4 according to an example embodiment.

Thus, referring to FIG. 5, using the arrangement that is depicted in FIG. 4, a technique 250 may be employed for purposes of generating an indicator for a parameter that is associated with a target. Pursuant to the technique 250, an optical emitter is used to produce an $R_{11}+C_{11}$ measurement acquired by a first optical receiver and to produce an a $R_{12}+C_{12}$ measurement, which is acquired by a second optical receiver, pursuant to block 254. A ratio of the $R_{11}+C_{11}$ measurement to the $R_{12}+C_{12}$ measurement is determined, pursuant to block 262. Also, according to the technique 250, a baseline ratio of $C_{11}/C_{12}$ is determined, pursuant to block 266. Using the detection and baseline ratios, a double ratio may then be determined, pursuant to block 270. An indicator for a parameter that is associated with the target may then be determined (block 274) by comparing the double ratio to a threshold.

Other variations are contemplated and are within the scope of the appended claims. For example, although FIGS. 2 and 4 depict exemplary ways to use multiple optical paths to determine a double ratio and derive a corresponding indicator, other optical paths and associated measurement systems may be used, in accordance with other embodiments. In this manner, in general, at least one emitter and at least one receiver may be used for purposes of establishing and using multiple optical paths to acquire the measurements. For example, in another non-limiting example, two different optical emitter-receiver pairs may be used to acquire measurements along two different optical paths. For the arrangement that is depicted in FIG. 2, the emitters 14-1 and 14-2 may be broad beam and narrow beam LEDs, respectively, which are both oriented in parallel to the normal to the substrate 102. In some embodiments, selective inking on the window 18 (see FIG. 1) and identical or different LEDs for the emitters 14 may be employed. In this matter the selective inking may be used to configure one of the LEDs to reflect relatively more light on the target 8 and the other LED to reflect relatively more light on the optical detector 10. In some embodiments, at least one optical emitter and at least one optical receiver may be used to acquire measurements along more than two optical paths.

Figure 6:
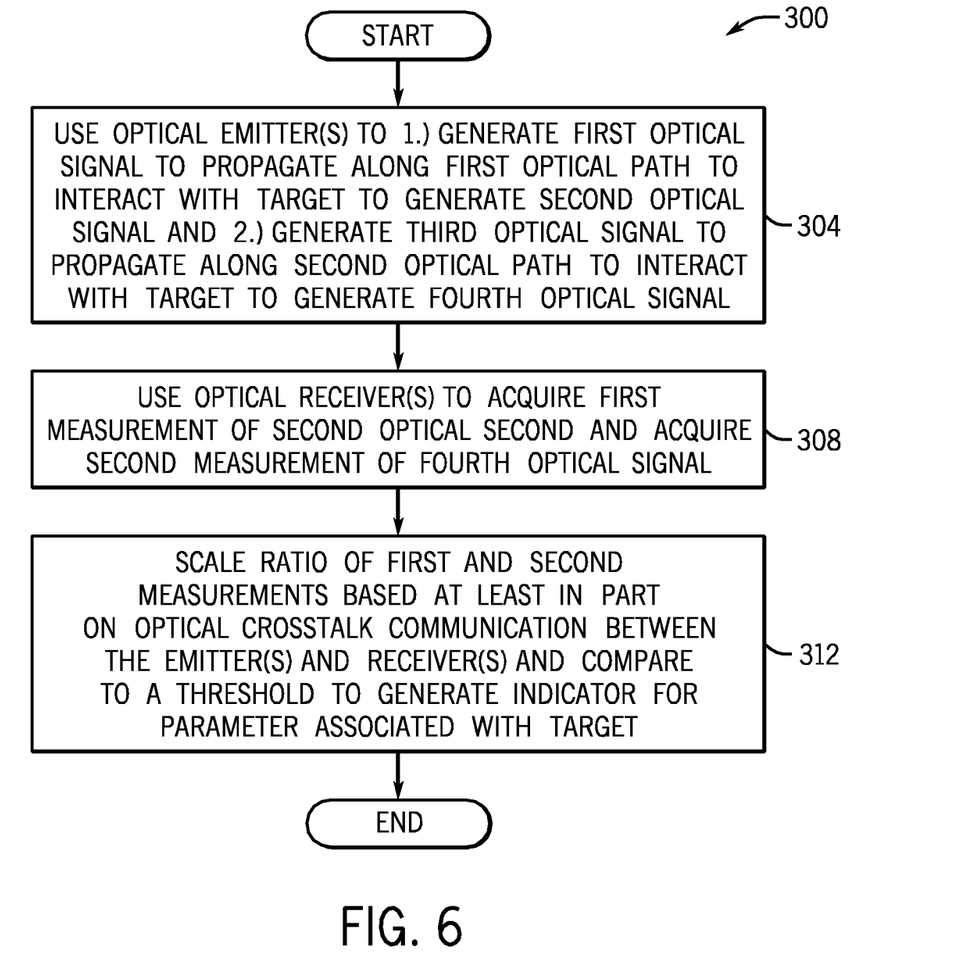
FIG. 6 is a flow diagram depicting a technique to determine a parameter that is associated with an object using an optical detector according to an example embodiment.

Thus, referring to FIG. 6, in general, a technique 300 may be used, in accordance with example embodiments. Pursuant to the technique 300, at least one optical emitter is used to 1. generate a first optical signal to propagate along a first optical path to interact with a target to generate a second optical signal, and 2. generate a third optical signal to propagate along a second optical path to interact with the target to generate a fourth optical signal. Pursuant to the technique 300, at least one receiver is used (block 308) to acquire a first measurement of the second optical signal and acquire a second measurement of the fourth optical signal. A ratio of the first and second measurements is then scaled (block 312) based at least in part on optical crosstalk communication between the emitter(s) and the receiver(s) along two or more different optical paths and compared to a threshold to generate an indicator for a parameter that is associated with a target.

Referring back to FIG. 1, the optical detector 10 may have one of many different architectures, depending on the particular embodiment. As a non-limiting example, in accordance with an exemplary embodiment, the optical detector 10 includes a housing 44, which contains the emitter(s) 14 and the receiver(s) 30. The optical detector 10 may also contain the window 18 for purposes of emitting and receiving light associated with the functions of the optical detector 10. The window 18 may contain an optical filter that selects an infrared or visible band for the receiver(s) 30, or alternatively, optical filter(s) may be placed over the receiver(s) 30. As another example, optical filter(s) may be placed over the receiver(s) 30, and another optical filter may be part of the window 18.

The optical detector 10 may include an integrated circuit 50, which contains various components to control the emitter(s) 14 for purposes of emitting light for the distance or particle density measurements as well as measure signals produced by the receiver(s) 30 when measuring the optical signals. To this end, the integrated circuit 50 may include, for example, the optical receiver(s) 30 (such as one or more photodiodes, for example) and a receive path that includes an analog-to-digital converter (ADC) 54. A multiplexer 52 of the receive path may be operated in a time multiplexed fashion to selectively couple an input of the ADC 54 to the receiver(s) 30 for purposes of receiving analog signals from the receivers 30. The ADC 54 generates a digital signal that is indicative of the analog signal, and this digital signal is received by a controller 58 of the integrated circuit 50.

In general, the controller 58, which may contain a processor, such as a microprocessor or microcontroller unit (MCU), or be formed from hardwired or programmable circuitry, processes the digital signal that is provided by the ADC 54 to determine one or more of the following: the detection ratio, the baseline ratio, the double ratio and the indicator for the parameter that is associated with the target 8. For purposes of determining the baseline ratio, the controller 58 may retrieve one or more calibration values (indicative of the optical crosstalk communication components) from a memory of the optical detector 10, such as a register 80, for example. It is noted that the calibration values 84 may be programmed by the manufacturer of the integrated circuit 50, may be programmed by the manufacturer of the optical detector 10, may be programmed by a system manufacturer that incorporates the optical detector 10 into a product, etc., depending on the particular embodiment. Depending on the particular embodiment, the calibration value(s) 84 may be the indirect and direct optical crosstalk components; combined indirect and direct optical crosstalk components for different emitter-receiver pairs; baseline ratios for different emitter-receiver pairs; and so forth.

Among its other features, in accordance with some exemplary embodiments, the integrated circuit 50 may include one or more drivers 60 (LED drivers, for example, as depicted in FIG. 1) for purposes of controlling the emission of optical energy by regulating the operation of the emitter(s) 14 in response to a signal from the controller 58. In this manner, the driver (60) may create the optical paths disclosed herein in a time-multiplexed fashion. Moreover, as shown in FIG. 1, in accordance with some exemplary embodiments, the controller 58 may communicate with an external bus 87 (a system management bus (SMB) or an inter-integrated (I²C) bus, as non-limiting examples) via a bus interface 64. In this manner, in accordance with some embodiments, the bus interface 64 may be programmed via external circuitry for purposes of programming the measurements to be performed by the optical detector 10; programming the calibration values 84; programming thresholds to which the double ratio is compared; and so forth. The bus interface 64 may be used to communicate data to and from the optical detector 10 over the external bus 87, which is indicative of one or more of the following: an indicator of the distance D or particle density, the baseline ratio, the detection ratio, and so forth.

Other variations are contemplated and are within the scope of the appended claims. For example, in some embodiments, the receiver(s) 30 may not be part of the integrated circuit 50. As another example, in accordance with other embodiments, the optical detector 10 may form a triangulated system that generates indicators of at least two distances with respect to the optical detector 10 such that a two-dimensional relationship of the target 8 with respect to the optical detector 10 may be determined.

Figure 7:
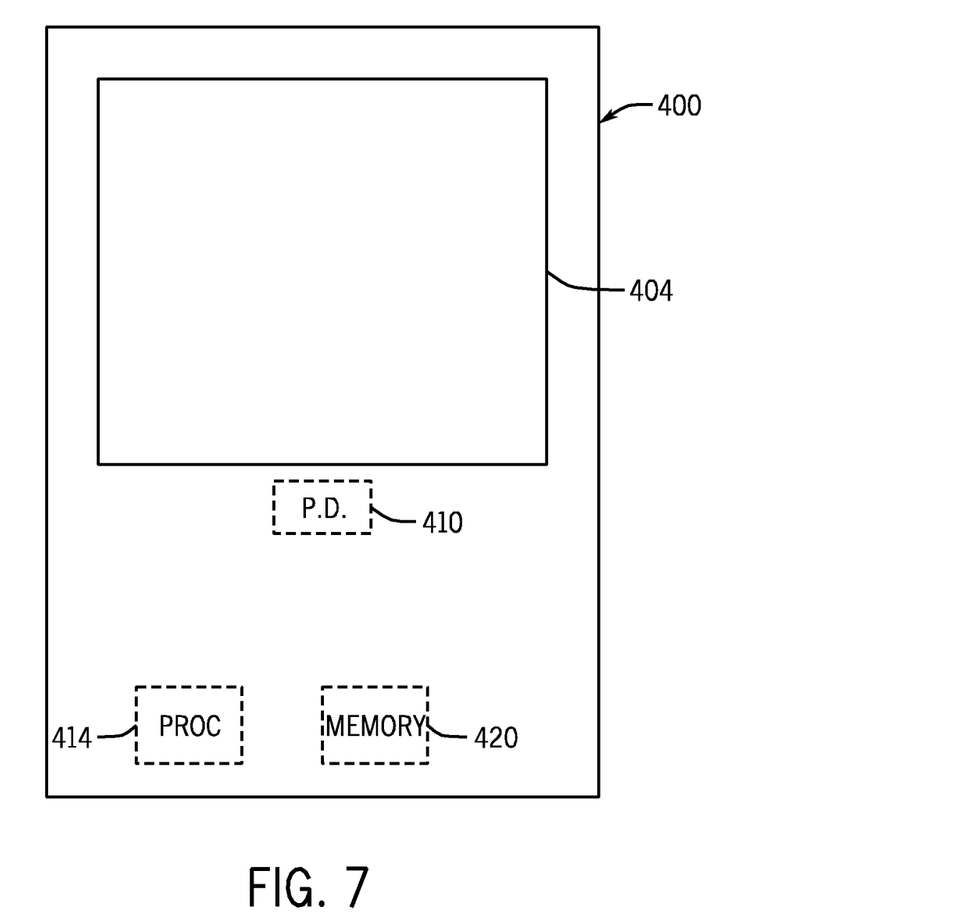
FIG. 7 is an illustration of a portable electronic device according to an example embodiment.

Such a relationship may be useful, for example, for a portable electronic device 400 (a tablet, a cellular telephone, a smart phone, a book reader, etc.) that is depicted in FIG. 7. In this regard, in accordance with an example embodiment, the portable electronic device 400 may employ a proximity detector 410 that has a similar design to the optical detector 10 (see FIG. 1) for purposes of allowing a user to interact with the device 400 so that the proximity detector 410 furnishes an indication of one or more distances to a target (a user's finger, for example). In general, the proximity detector 410, regardless of the number of emitters and receivers, employs techniques disclosed herein, such as techniques 150, 250 and/or 300, for purposes of generating an indication of at least one distance between the target and the proximity detector 410.

For example, in an example embodiment, the proximity detector 410 may store optical crosstalk calibration values and use the calibration values as described herein to generate indications of at least two distances such that a two dimensional screen location of a stylus or a user's finger with respect to a screen 404 of the electronic device 400 may be tracked for purposes of allowing a user to make selections and input data. As shown in FIG. 7, the electronic device 400 may be a processor-based machine, which contains at least one processor 414 (one or more central processing units (CPUs) or microcontrollers, as non-limiting examples), a non-transitory storage memory 420 (a semiconductor memory, for example), etc.

While a limited number of embodiments have been disclosed herein, those skilled in the art, having the benefit of this disclosure, will appreciate numerous modifications and variations therefrom. It is intended that the appended claims cover all such modifications and variations.

What is claimed is:

1. A method comprising:
using at least one emitter to generate a first optical signal to propagate along a first optical path to interact with a target to generate a second optical signal and generate a third optical signal to propagate along a second optical path to generate a fourth optical signal;
using at least one receiver to acquire a first measurement of the second optical signal and acquire a second measurement of the fourth optical signal; and
generating an indication of a parameter associated with the target, the generating comprising scaling a first ratio of the first and second measurements based at least in part on optical communication between the at least one emitter and the at least one receiver that does not involve interaction with the target.

2. The method of claim 1, wherein
the one emitter comprises a first emitter and a second emitter;
at least one receiver comprises a first receiver;
the generating further comprises determining a second ratio of a first measurement of optical crosstalk communication between the first emitter and the first receiver to a second measurement of optical crosstalk communication between the second emitter and the first receiver; and
the scaling further comprises determining a third ratio of the first ratio to the second ratio.

3. The method of claim 1, wherein
the at least one emitter comprises a first emitter;
the at least one receiver comprises a first receiver and a second receiver;
the generating further comprises determining a second ratio of a first measurement of optical crosstalk communication between the first emitter and the first receiver to a second measurement of optical crosstalk communication between the first emitter and the second receiver; and
the scaling further comprises determining a third ratio of the first ratio to the second ratio.

4. The method of claim 1, wherein
the parameter comprises a particle density of the target or a distance to the target.

5. The method of claim 1, wherein the optical communication comprises an optical crosstalk communication.

6. The method of claim 1, wherein the generating further comprises comparing the scaled first ratio to a threshold to generate the indication of the parameter.

7. The method of claim 1, wherein
the at least one emitter comprises a first emitter and a second emitter;
the at least one receiver comprises a first receiver; and
the generating is further based on a first measure of indirect and direct crosstalk communication between the first emitter and the first receiver and a second measure of indirect and direct crosstalk communication between the second emitter and the first receiver.

8. The method of claim 1, wherein
the at least one emitter comprises a first emitter;
the at least one receiver comprises a first receiver and a second receiver; and
the generating is further based on a first measure of indirect and direct crosstalk communication between the first emitter and the first receiver and a second measure of indirect and direct crosstalk communication between the first emitter and the second receiver.

9. The method of claim 1, further comprising storing in the optical detector at least one calibration value associated with the optical communication that does not involve interaction with the target.

10. An optical detector comprising:
at least one emitter to:
generate a first optical signal to propagate along a first optical path to interact with an object to generate a second optical signal; and
generate a third optical signal to propagate along a second optical path other than the first optical path to generate a fourth optical signal;
at least one receiver to:
acquire a first measurement of the second optical signal; and
acquire a second measurement of the fourth optical signal; and
a controller to scale a first ratio of the first and second measurements based at least in part on at least one additional measurement acquired by the at least one receiver which does not involve interaction with the object to generate an indication of a parameter associated with the object.

11. The optical detector of claim 10, wherein the controller is adapted to compare the scaled first ratio to a threshold to generate the indication.

12. The optical detector of claim 10, wherein
the controller is adapted to scale the first ratio based on a second ratio of measurements acquired by the at least one receiver in the absence of the object.

13. The optical detector of claim 12, wherein the controller is adapted to store data indicative of the second ratio.

14. The optical detector of claim 10, wherein
the parameter comprises a particle density of the target or a distance to the object.

15. The optical detector of claim 10, wherein at least one additional measurement comprises a measurement of optical crosstalk communication between the at least one receiver and the at least one emitter.

16. An apparatus comprising:
an integrated circuit comprising:
a controller;
at least one driver adapted to use at least one emitter to generate at least one electrical signal to:
generate a first optical signal to propagate along a first optical path to interact with an object to generate a second optical signal; and
generate a third optical signal to propagate along a second optical path other than the first optical path to generate a fourth optical signal; and
at least one receiver adapted to receive at least one electrical signal indicative of a first measurement of the second optical signal and a second measurement of the fourth optical signal,
wherein the controller is adapted to scale a first ratio of the first and second measurements based at least in part on optical crosstalk communication between the at least one emitter and the at least one receiver to generate an indication of a parameter associated with the object.

17. The apparatus of claim 16, wherein
the parameter comprises a particle density of the object or a distance to the object.

18. The apparatus of claim 16, wherein optical crosstalk communication comprises at least one of an indirect optical communication between the at least one emitter and the at least one receiver in the absence of the object and a direct optical communication between the at least one receiver and the at least one emitter in the absence of the object.

19. The apparatus of claim 16, wherein
the at least one emitter comprises a first emitter;
the at least one receiver comprises a first receiver and a second receiver; and the controller is adapted to:
determine a second ratio of a first measurement of optical crosstalk communication between the first emitter and the first receiver to a second measurement of optical crosstalk communication between the first emitter and the second receiver; and
determine a third ratio of the first ratio to the second ratio to scale the first ratio.

20. The apparatus of claim 16, wherein
the least one driver is adapted to drive a first emitter to generate the first optical signal and drive a second emitter to generate the third optical signal; and
the receive path is adapted to:
receive a first electrical signal generated in response to optical energy sensed by an optical receiver and indicative of the first measurement of the second optical signal; and
receive a second electrical signal generated in response to optical energy sensed by the optical receiver and indicative of the second measurement of the fourth optical signal.

* * * * *